United States Patent [19]

Reynard et al.

[11]  4,257,917
[45]  Mar. 24, 1981

[54] CATALYST FOR PREPARATION OF SOLUBLE POLY(DICHLOROPHOSPHAZENES)

[75] Inventors: Kennard A. Reynard; Arthur H. Gerber, both of Cleveland, Ohio

[73] Assignee: The Firestone Tire & Rubber Company, Akron, Ohio

[21] Appl. No.: 958,585

[22] Filed: Nov. 7, 1978

Related U.S. Application Data

[62] Division of Ser. No. 758,740, Jan. 12, 1977, Pat. No. 4,139,598, which is a division of Ser. No. 474,055, May 28, 1974, Pat. No. 4,005,171.

[51] Int. Cl.$^3$ ............................................. B01J 27/14
[52] U.S. Cl. .................................. 252/435; 252/428; 252/437; 260/543 P; 260/941; 423/299; 423/300

[58] Field of Search ................ 423/300, 299; 252/428, 252/435; 260/543 P, 941

[56] References Cited

U.S. PATENT DOCUMENTS

| | | | |
|---|---|---|---|
| 3,625,755 | 12/1971 | Potrafke | 252/428 X |
| 4,005,171 | 1/1977 | Reynard et al. | 423/300 X |
| 4,139,598 | 2/1979 | Reynard et al. | 423/300 |

*Primary Examiner*—Helen M. S. Sneed

[57] ABSTRACT

High molecular weight poly(dihalophosphazenes) which exhibit solubility in benzene and in substituted benzenes are prepared in solution or in bulk from dihalophosphazenes such as $(Cl_2PN)_{3-7}$ at moderate temperatures by the use of novel polymerization catalysts.

9 Claims, No Drawings

CATALYST FOR PREPARATION OF SOLUBLE POLY(DICHLOROPHOSPHAZENES)

This is a division of application Ser. No. 758,740, filed Jan. 12, 1977, now U.S. Pat. No. 4,139,598, which is a division of Ser. No. 474,055, filed May 28, 1974, now U.S. Pat. No. 4,005,171.

This invention relates to the preparation of poly(dichlorophosphazene) which is soluble in various solvents including benzene, chlorobenzenes, toluene and mixtures of such solvents.

More specifically it relates to the polymerization of dichlorophosphazene of the formula $(Cl_2PN)_{3-7}$ to polymers of the formula $[Cl_2PN]_{20-50,000}$ wherein the polymerization is accomplished in solution or in bulk in the presence of one or more catalysts.

Uncatalyzed bulk polymerization of $(Cl_2PN)_3$, $(Cl_2PN)_4$, or mixtures thereof, to form soluble $[Cl_2PN]_n$ polymer is described in U.S. Pat. No. 3,370,020. This process employs temperatures of 200°–300° C., preferably about 250° C.

Another known process for producing soluble poly(dichlorophosphazenes) is described in Example 1 of U.S. Pat. No. 3,515,688 and elsewhere in the literature. This is essentially a batch process in which cyclic trimeric $(Cl_2PN)_3$ is heated in a sealed tube under an inert atmosphere for a stated time at polymerizing temperatures.

A simpler process for the large scale production of soluble $[Cl_2PN]_n$ polymer in good yield is desired because this polymer can be converted to useful phosphazene derivatives as described for example, in recently issued U.S. Pat. Nos. 3,370,020; 3,515,688; 3,700,629 and 3,702,629 and elsewhere.

The primary object of this invention is to provide a simple process for the preparation of soluble, high molecular weight $[Cl_2PN]_n$ polymer at a significantly lower temperature than currently practiced in the art, said polymer having an intrinsic visosity of about 0.01 to about 3.0 dl/g(benzene, 30° C.), and a solubility in benzene, toluene, xylene, chlorobenzene and o-dichlorobenzene.

Another object of this invention is to provide novel cyclic phosphazene polymerization catalysts useful in the above process and a method for their preparation.

Still another object of this invention is to form the $[Cl_2PN]_n$ polymer by a process in which the polymer produced is ready for reaction or purification immediately following polymerization, thereby avoiding the delay normally encountered when high molecular weight materials are dissolved.

These and other objects, which will be apparent from the description which follows, are achieved by the use of specific catalysts which make possible the polymerization of cyclic phosphazene in solution or in bulk to form the desired poly(dichlorophosphazene) polymer.

The catalyzed polymerization when conducted in accordance with this invention is conducted with ease in solution or in bulk and at temperatures which are significantly lower than those previously employed. The use of lower temperatures results in a more efficient polymerization and also diminish the tendency to form gel.

For solution or bulk polymerization any convenient pressure can be used from vacuum up to atmospheric pressures and above. Vaporization of starting monomer(s) in systems which are not closed, can be repressed by employing 10 weight % or even less or a suitable solvent. Previously reported bulk polymerizations at elevated temperature under atmospheric conditions have been attended by significant vaporization of monomer(s) with concurrent change of monomer(s) to catalyst ratio, conditions undesirable for reproducibility and molecular weight control. Other general advantages of a solution polymerization process are that viscosity is more readily controlled and good agitation can be accomplished in very inexpensive equipment.

Still another important advantage in an atmospheric solution polymerization process is that the $[Cl_2PN]_n$ polymer so produced can be purified immediately or can be utilized directly for subsequent derivatization as in its reaction with alkoxide, fluoroalkoxide, or aryloxide salts, or mixtures thereof.

Other advantages of the polymerization process of this invention will become evident when the process is compared with the known art which relates to the bulk polymerization of hexachlorophosphazene, $(Cl_2PN)_3$, octachlorophosphazene, $(Cl_2PN)$, and mixtures thereof as described, for example, in Allcock, "Phosphorus-Nitrogen Compounds", Academic Press, N.Y., 1972 and Chem. Reviews, 72, 315 (1972). The bulk polymerizations reported in the prior art are conducted under vacuum and have further disadvantages. For example, high temperatures (220°–350° C.) are required, nonreproducible products are obtained, spurious formation of gelled polymer (particularly at moderate to high conversions) is experienced, molecular weight is difficult to control, and a product with a high degree of polydispersity is obtained.

By the polymerization process of this invention the polymerization of cyclic compounds having the formula $(X_2PN)_m$, where m is a whole positive integer of from 3 to 7 inclusive and X is a halogen selected F, Cl, Br and both X's are not required to be identical, is accomplished at temperatures from about 130°–220° C. in solution or about 130°–200° C. in bulk for periods ranging from 1 hour to several days at any suitable pressure between vacuum and superatmospheric pressure.

For solution polymerization the concentration of monomer can vary from about 5–95%. Preferred solvents for solution polymerization are those which are unreactive to both catalyst and $(X_2PN)_m$ monomer and which preferably are solvent for both monomer and polymer at polymerization temperature. Suitable solvents include nitro or halo aromatics such as chlorobenzene, 1,2-dichlorobenzene, 1,2,4-trichlorobenzene, bromobenzene, m- or p-bromochlorobenzene, nitrobenzene, o- or m-nitrotoluene, m-chloronitrobenzene, and mixtures of these solvents. These and other solvents which may also be employed singly or in combination include benzene, biphenyl, toluene, xylene, halogenated biphenyls, carbon tetrachloride, hexachloroethane, tetrachloroethane, pentachloroethane, and hexachlorobutadiene. The methylated benzenes are preferably used at temperatures below 195° C. and benzene and biphenyl are preferably used at temperatures below 220° C.

When the polymerization is conducted at atmospheric pressure or above, a dry inert atmosphere such as nitrogen, help us, or argon is preferably employed. Polymerizations may be conducted under vacuum or under pressure. The concentration of catalyst(s) can vary from 0.1–20% but is preferably in the range of 0.1–5%.

Conversions of up to about 80% of soluble $[Cl_2PN]_n$ polymer have been achieved wherein the polymer is characterized by an intrinsic viscosity as measured in benzene at 30° C. of from about 0.01 to about 3.0 dl/g. High percent conversions to polymer are favored by an increase in temperature, catalyst(s) concentration, monomer concentration, and polymerization time. The $[Cl_2PN]_n$ polymer so produced is characterized by very little or no gelled material and is thus, ideally suited for the subsequent preparation of other substituted polyphosphazenes which have a wide range of utility.

Although polymerizations are preferably carried out with compounds of formula $(Cl_2PN)_m$, polymerization of fluoro-, bromo-, and even mixed halo- cyclophosphazenes have been effected. In general, the fluoro derivatives require higher polymerization temperatures and the bromo derivatives require lower polymerization temperatures than those used to polymerize the corresponding chloro derivatives.

The catalysts employed in the practice of the polymerization process of this invention to form soluble, high molecular weight $[Cl_2PN]_n$ polymer are selected from three groups, namely metal or organo metal salts derived from very strong acids (Group A), strong acids (Group B), and derivatives of halocyclicphosphazenes (Group C). Catalysts may be employed singly or in combination.

Representative members from each group include the following:

Group (A): comprises metallic or quaternary ammonium salts in which the anion is selected from the group consisting of:

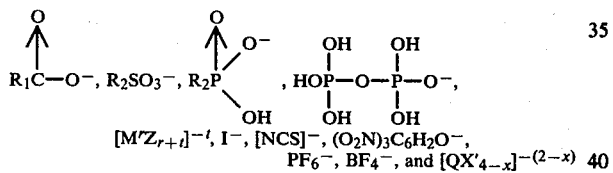

where $R_1$ is a monovalent member selected from the group consisting of polyhaloalkyl where the halogen is F, Cl or mixtures thereof, perfluoroaryl and perchloroaryl; $R_2$ is a monovalent member selected from the group consisting of F, Cl, lower alkyl ($C_1$–$C_5$), aryl, substituted alkyl and substituted aryl with the proviso that $R_2$ is not halogen when bonded to

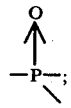

Z is F or Cl; M is a metal selected from Groups Ia, Ib, IIa, IIb, and VIII of the Periodic Table, Pb, Mn, or Th; r is the valence of Metal M; t is in integer designating the magnitude of the negative charge of the complex ion $[M^rZ_{r+t}]^{-t}$; and Q is a metal selected from the group consisting of Hg, Cd and Zn and $X'$ is either Br or I; and x is 0 or 1.

The following are representative as examples of specific catalysts of Group (A):

1. Sulfonic acids where $R_2$ (above) includes the following:
lower alkyl (methyl through butyl)
perfluoromethyl
perfluorophenyl
fluoro-
chloro-
phenyl-
toluoyl-
naphthyl-
P-bromophenyl-
nitrophenyl-
2,4-dinitrophenyl-
biphenyl-
m-(HO$_3$S)phenyl- 2. Polyhalocarboxylic acids where $R_1$ (above) includes the following:
trifluoromethyl-
trichloromethyl-
difluoremethyl-
difluorochloromethyl-
perfluoropropyl-
perfluorobutyl- 3. Salts of miscellaneous acids:
fluoboric
fluophosphoric
picric
phosphoric
pyrophosphoric
polyphosphoric
hydriodic (alkali, alkaline earth and quaternary ammonium salts only)

4. Salts where the anion is a complex polyhal are represented by the formula $[M^rZ_{r+t}]^{-t}$ where M is a metal or non-metal ion having a valence of r and is selected from Al, As, Fe, Mo, V, Nb, Ta, Pd, Pt, Re, Rh, Ti, Zr, Sb, Sn; Z is F or Cl; and t is an integer designating the magnitude of the negative charge of said complex ion. Representative complex negative ions are $SbF_6^-$, $SbCl_6^-$, $AsF_6^-$, $AlF_6^{-3}$, $FeF_6^{-3}$, $TiF_6^{-2}$, and $MoCl_6^{-3}$.

5. Alkaline and alkaline earth salts having an anion represented by the formula $[QX'_{4-x}]^{-(2-x)}$ where x is zero or 1; Q is selected from Hg, Zn, Cd; and $X'$ is bromine or iodine.

Preferred cations for all the catalyst salts of this invention are Li, Na, K, Mg, Ba, Hg, Ag, and quaternary ammonium ions.

Group (B): comprises the strong acids of Group (A), i.e., the sulfonic acids and polyhalocarboxylic acids used to prepare the metal salt catalysts of Group (A), picric acid, and in addition $H_3PO_4$ and the dehydrated derivatives of $H_3PO_4$ such as pyrophosphoric acid, $P_2O_5$ and $P_2O_5$-$H_3PO_4$ mixtures, usually designated "polyphosphoric acid".

Group (C): comprises substituted cyclophosphazenes represented by the formula $(X)_y(PN)_m(An)_x$, where m is a positive integer of 3 to 7; x and y are positive integers the sum of which equals 2m; x being at least one and y being not less than zero; each X is a halogen selected from F, Cl, or Br; An represents an anion described in Group (A) above, and all the An groups need not be identical to other An groups present in the cyclophosphazene and for cyclophosphazenes containing two or more X's, all of the X's need not be identical.

The catalysts of Groups A, B, and C may be employed singly, in combination, or as mixtures with non-catalyst metal halide salts such as LiCl, LiBr, $MgCl_2$, $MgBr_2$, $HgCl_2$, $HgBr_2$, which may be added for the purpose of modifying the polymerization.

The phosphazene derivatives of Group (C) are prepared by substitution reactions of $X_6P_3N_3$ or $X_8P_4N_4$, or mixtures thereof, or mixtures with higher oligomers, wherein X is a halogen as described above, with one or more of the salts described in Group (A). Preferred cations of the salt are silver, alkali metal, mercury and quaternary ammonium. The interchange is accomplished at temperatures from about 25° C. to 130° C., or even higher, providing the temperature is such that little or no polymerization occurs, and reaction times of about 1 hour to several days have been used. The reaction is preferably carried out in a dry polar aprotic solvent such as organic ethers [e.g. tetrahydrofuran, 1,2-dimethoxyethane, 1,4-dioxane, bis(2-methoxyethyl)ether], alkylnitriles (e.g. $CH_3ON$, $C_3H_7ON$), nitroalkanes (e.g. $CH_3NO_2$, $C_2H_5NO_2$, $t-C_4H_9NO_2$), nitrobenzene and nitrotoluene, and mixtures thereof, but less polar solvents such as benzene, toluene and their ring chlorinated or brominated derivatives may also be employed. Polar solvents such as N,N-dimethylformamide, N,N-dimethylacetamide, N-methylpyrrolidinone, and hexamethylphosphoramide may also be used singly or in combination with the above solvents provided that reaction temperatures are maintained below 50° C.

The phosphazene derivatives prepared as above decribed, can be freed of insoluble salt and used directly for the solution polymerization process of this invention, provided the are in a suitable solvent for polymerization, or they may be isolated and then used for polymerization of halophosphazene oligomers, or mixtures thereof. Isolation and purification are carried out by methods well known in the art.

The cyclophosphazene derivatives are advantageous as polymerization catalysts because they afford homogeneous polymerizations and more importantly may afford $[Cl_2PN]_n$ polymer with low polydispersity.

In the polymerization process of this invention monomer, catalyst, and solvent (if employed), are brought together at an appropriate temperature under an inert atmosphere. Suitable methods include: (1) prereacting the entire polymerization mixture at a temperature below the desired polymerization temperature to form in situ a compound of Group (C), and then continue polymerization at the desired polymerization temperature; (2) identical to method (1) except there is no separately conducted prereaction at a lower temperature; and (3) prereacting a limited amount of monomer, with a salt of Group (A), adding the remainder of monomer, and solvent, if any, and heating at the desired polymerization temperature. Incremental additions of catalyst, monomer, or both, may be made in the practice of any of the above polymerization methods.

The remarkable catalytic activity shown by the very strong acids utilized in this invention was unexpected in view of the results reported with hydrogen chloride. It has been found that bulk polymerizations of $(Cl_2PN)_3$ in the presence of HCl ($\geq 1$–$5 \times 10^{-3}$ weight %) at 250–270° C. are not only retarded in rate but afford lower molecular weight $[Cl_2PN]_n$ polymer than polymerizations conducted in the absence of HCl, whereas polymerizations using the strong acid catalysts of this invention have been successfully conducted at considerably lower temperatures (150°–190° C.). It has been found that essentially no polymerization occurred when benzoic acid was employed under conditions which gave significant polymerization with the acid catalysts of this invention.

Not all strong acids and their salts are active catalysts for the polymerization of cyclic $(Cl_2PN)_3$ to soluble $[Cl_2PN]_n$ polymer. For example, HCl, HBr, $HgCl_2$ and $HgBr_2$ are not catalysts when employed by themselves.

The following examples are not intended to limit the invention in any way, but are merely exemplary of preferred embodiments of the invention.

EXAMPLES 1–38

A dry Pyrex test tube (200×25 mm) was charged with a stirring bar, catalyst, $(Cl_2PN)_3$ monomer (10–20 g, vacuum distilled and recrystallized from n-heptane), and solvent (50 weight %), unless indicated otherwise. The reaction mixture was purged with dry nitrogen and heated under $N_2$ one hour at 150°–155° C. prior to reaching polymerization temperature, unless indicated otherwise. Intrinisc viscosities ($[\eta]$, dl/g) of soluble polymer were run in dry benzene at 30° C. and % conversion to polymer was determined by vapor-phase-liquid chromatography. The solvents employed were either (A) a 2:1 (by weight) mixture of 1,2-$Cl_2C_6H_4C_6H_5NO_2$, (B) 1,2,4-$Cl_3C_6H_3$, or (C) 1,2-$Cl_2C_6H_4$. The results are shown in Examples 1–38.

| Ex. | Catalyst (weight % on Monomer) | Solvent(s) | Polymerization Conditions °C. | Hrs. | Remarks |
|---|---|---|---|---|---|
| 1 | None | A | 190 | 15 | No Polymer |
| 2 | $(CF_3SO_3)_2Hg[1\%]$ | B | 217 | 3 | Soluble polymer $[\eta] = 1.4$ |
| 3 | $(CF_3SO_3)_2Hg[1\%]$ | A | 190 | 6½ | Soluble polymer |
| 4 | $(CF_3SO_3)_2Hg[1\%]$ | C | 190 | 10 | Soluble polymer |
| 5 | $(CF_3SO_3)_2Hg(0.3\%)$ | B (75%) | 217 | 3 | Soluble polymer $[\eta] = 2.7$ |
| 6 | $CF_3SO_3Ag(1\%)$ | A | 190 | 6½ | Soluble and gelled polymer |
| 7 | $AgPF_6(3\%)$ | A | 190 | 7 | Soluble polymer low conversion |
| 8 | $(C_6F_5SO_3)_2Ba(1\%)$ | A | 190 | 4 | Soluble polymer |
| 9 | $[2,4-(NO_2)_2-C_6H_3SO_3]_2Mn(1\%)$ | A | 190 | 4 | Soluble polymer |
| 10 | $KSbCl_6(1\%)$ | A | 190 | 6 | Soluble Polymer |
| 11 | $Co(BF_4)_2(1\%)$ | A | 190 | 6 | Soluble polymer |
| 12 | $CF_3CO_2Ag(2\%)$ | A | 190 | 6½ | 12% Conversion $[\eta] = 0.20$ |
| 13[b] | $HgI_2(2\%) +$ NaI (0.7%) | C | 190 | 7 | 19% Conversion |
| 14 | $HgI_2(2\%) +$ NaI (0.7%)[c] | C | 190 | 11 | 2% Conversion (prior to addition of NaI) |
| 15 | NaI(2%) | C | 190 | 10½ | 13% Conversion |

-continued

| Ex. | Catalyst (weight % on Monomer) | Solvent(s) | Polymerization Conditions °C. | Hrs. | Remarks |
|---|---|---|---|---|---|
| 16 | $C_6H_5SO_3^{\ominus}(CH_3)_4N^{\oplus}$ (2%) | A | 190 | 11 | 51% Conversion, $[\eta] = 0.06$ |
| 17 | $Li_2TiF_6$(2%) | A | 190 | 6 | 25% Conversion |
| 18 | $CF_3SO_3Na$(2%) | A | 190 | 10 | 10% Conversion |
| 19 | $(CH_3SO_3Hg)_2O$(2%) | A | 190 | 2½ | 61% Conversion $[\eta] = 0.31$ |
| 20 | $(CH_3SO_3Hg)_2O$ (0.5%) | A | 190 | 15 | 24% Conversion $[\eta] = 0.75$ |
| 21 | $(CH_3SO_3Hg)_2O$(2%) | A | 150–155 | 17½ | Soluble Polymer |
| 22 | $C_6H_5HgOSCH_3$(2%) (with O above and below S) | A | 190 | 2½ | 40% Conversion |
| 23 | $(CH_3SO_3)_2Zn$(2%) | A | 190 | 10 | 7% Conversion |
| 24 | $CH_3SO_3H$(2%) | A | 190 | 6½ | 21% Conversion |
| 25 | $CH_3SO_3H$(2%)+ LiCl(1%) | A | 190 | 6½ | 24% Conversion |
| 26 | $C_6F_5CO_2H$(2%) | A | 190 | 40 | 53% Conversion |
| 27 | $CF_3SO_3H$(2%) | A | 190$^{(d)}$ | 4 | Soluble Polymer |
| 28 | $Cl_3CCO_2H$(2%) | A | 190 | 8 | 30% Conversion |
| 29 | $n$-$C_3F_7CO_2H$(2%) | A | 150–155 | 25 | 15% Conversion |
| 30 | $n$-$C_7F_{15}CO_2H$(2%) | A | 190 | 13 | 36% Conversion |
| 31 | $P_2O_5$(2%) | A | 190 | 26 | 63% Conversion, $[\eta] = 0.24$ |
| 32 | polyphosphoric acid (2%) | A | 190 | 23 | 47% Conversion, $[\eta] = 0.55$ |
| 33 | polyphosphoric acid (2%) | C | 190 | 24 30 | 43% Conversion 60% Conversion, $[\eta] = 0.15$ |
| 34 | polyphosphoric acid (2%) + LiCl (2%) | C | 190 | 24 | 15% Conversion |
| 35 | KNCS (2%) | A | 190 | 25 | 40% Conversion, $[\eta] = 0.25$ |
| 36 | picric acid (2%) | A | 190 | 10 | Soluble Polymer |
| 37 | $ClSO_3H$ | A | 190 | 6 | Soluble Polymer |
| 38$^{(e)}$ | $(CF_3SO_3)_2Hg$ (2%) | $C_6H_6$ (90%) | 200 | 24 | Soluble Polymer |

$^{(a)}$Derivatized to $[(CF_3CH_2O)_2PN\cdot(HC_4F_8CH_2O)_2PN]_n$ by reaction when an equimolar mixture of $CF_3CH_2ONa$ and $HC_4F_8CH_2ONa$, $[\eta]$ 30° acetone = 1.0 di/8. Calcd: C, 23.5; H, 1.7; Cl, 0.0 Found: C, 22.2; H, 1.5; Cl, 0.1.
$^{(b)}$$NaHgI_3$ and $Na_2HgI_4$ formed in situ.
$^{(c)}$Added 11 hours after addition of $HgI_2$. Gelled polymer formed 10½ hours after addition of NaI.
$^{(d)}$Reaction heated 18 hours at 150° C. prior to heating to reflux.
$^{(e)}$Polymerization conducted in sealed tube under pressure.

EXAMPLES 39–42

The procedure of Example 1 was followed using the indicated monomer(s) and $(CH_3SO_3Hg)_2O$ (2% on monomer) as catalyst and 1,2-$Cl_2C_6H_4$-$C_6H_5NO_2$ (2w/1w) as solvent (50% concentration) at 190° C.

| Ex. | Monomer (% by weight) $(Cl_2PN)_3$ | $(Cl_2PN)_4$ | Polymerization Time (Hours) | Remarks |
|---|---|---|---|---|
| 39 | 25 | 25 | 4 | 27% Conversion, $[\eta] = 0.10$ |
| 40$^{(a)}$ | 25 | 25 | 11½ | 46% Conversion, $[\eta] = 0.07$ |
| 41 | 0 | 50 | 43 | 19% Conversion |
| 42 | 30 | 15 + 5% mixture of $(Cl_2PN)_5$, $(Cl_2PN)_6$ | 11½ | 40% Conversion |

$^{(a)}$LiCl(2%) present with the $(CH_3SO_3Hg)_2O$ catalyst.

EXAMPLES 43–50

The procedure of Example 1 was followed without any solvent. Polymerizations of Examples 43–50 were conducted in a sealed evacuated pyrex tube.

| Ex. | Catalyst (weight % on monomer) | Polymerization Conditions °C. | Hrs. | Remarks |
|---|---|---|---|---|
| 43 | None | 217 | 3 | No high polymer |
| 44 | $(CF_3SO_3)_2Hg$(3%) | 230–240 | 3 | Gelled polymer |
| 45 | $(CF_3SO_3)_2Hg$(0.5%) | 190 | 5 | Soluble polymer |
| 46 | $CF_3SO_3Ag$(1%) | 180 | 3 | Soluble polymer |
| 47 | $HgCl_2$(1%) | 250 | 8 | 24% Conversion, $[\eta]_{\phi H}^{30°\,C.} = 0.46$ dl/g. |
| 48 | $HgBr_2$(1%) | 250 | 8 | 29% Conversion, $[\eta]_{\phi H}^{30°\,C.} = 0.52$ dl/g. |
| 49 | HCl | 190 | 24 | No high polymer |
| 50 | polyphosphoric(1%) | 190 | 20 | Soluble polymer |

EXAMPLE 51

A 1-liter flask was charged under a nitrogen atmosphere with $(Cl_2PN)_3$ (450 g), o-dichlorobenzene (50 g), and polyphosphoric acid (3.0 g, Matheson Coleman & Bell Company). The mixture was heated with good agitation 1 hour at 150°–170° C. are then at about 195° C. for 45 hours to give a very viscous mixture. Unreacted $(Cl_2PN)_3$ was removed by extracting twice with 500 ml dry heptane, and then by stirring overnight at 40° C. with 500 ml dry petroleum ether. Solvent was decanted off and the $[Cl_2PN]_n$ polymer (184 g, 41% yield), which had an intrinsic viscosity of 0.9 dl/g (benzene, 30° C.), was dissolved in 500 ml dry benzene. This polymer solution was reacted with an equimolar mixture of $CF_3CH_2ONa$ and $HCF_2C_3F_6CH_2ONa$ in tetrahydrofuran for 1 day at room temperature to give, after purification, an elastomeric poly(fluoroalkoxyphosphazene) copolymer with an intrinsic viscosity 1.1 dl/g in acetone (30° C.) and a chlorine content of 0.03%.

EXAMPLES 52–53

Polymerization of $(Cl_2PN)_3$ Using Phosphazene Catalyst

EXAMPLE 52: Via $(Cl_2PN)_3$

The phosphazene catalyst was prepared by reaction, under dry nitrogen, of $(Cl_2PN)_3$ (3.0 g), $(CH_3SO_3Hg)_2$ (0.5 g), in nitrobenzene (7.5 g) for 4 hours at 135° C. The mixture was cooled to room temperature and insoluble solids removed by centrifuging. An aliquot (4.0 g) of the clear yellow liquor was added to $(Cl_2PN)_3$ (13.8 g) and 1,2-$Cl_2C_6H_4/C_6H_5NO_2$ (2w/1w, 12.2 g) which was polymerized under nitrogen for 6½ hours at 190° C. The $[Cl_2PN]_n$ polymer which was produced (53% yield by vapor-phase-liquid chromatography) had an intrinsic viscosity of 0.40 dl/g (benzene, 30° C.).

EXAMPLE 53: Via $(Cl_2PN)_4$

The phosphazene catalyst was prepared by reaction, under dry nitrogen, of $(Cl_2PN)_4$ (3.0 g, 6.5 mmol), $CF_3CO_2Ag$ (4.0 g, 18.0 mmol) in nitrobenzene (18 g) for 2 hours at 75° C. The immobile mass was shaken with 1,2-$Cl_2C_6H_4$ (36 g) and solids removed by subsequent centrifuging. An aliquot (7.5 g) of the clear light yellow solution was added to $(Cl_2PN)_3$ (15 g) and 1,2-$Cl_2C_6H_4/C_6H_5NO_2$ (2w/1w, 7.5 g) which was polymerized under nitrogen for 6 hours at 190° C. The $[Cl_2PN]_n$ polymer which was produced 29% yield) had an intrinsic viscosity of 0.22 dl/g (benzene 30° C.).

EXAMPLE 54

A mixture of $(CH_3SO_3Hg)_2O$ (0.3 g), $(Cl_2PN)_3$ (1.0 g), and nitrobenzene (5.0 g) was heated under nitrogen with stirring at 135° C. for 2 hours. Vapor-phase-liquid chromatography was indicative of a significant change in $(Cl_2PN)_3$ concentration mixture was added to additional $(Cl_2PN)_3$ (14.0 g) and o-dichlorobenzene and heated and gentle reflux (Ca. 190° C.) for 4 hours. Soluble polymer (33% conversion) was formed which had an intrinsic viscosity of 0.10 dl/g (benzene, 30° C.).

EXAMPLE 55

Preparation of a Poly(chloro-trifluoroacetoxy) Cyclophosphazene

To a solution of $(Cl_2PN)_3$ (2.5 g, 7.19 mmol) in dry tetrahydrofuran (50 ml) was added, with good stirring under nitrogen, silver trifluoroacetate (5.0 g, 22.6 mmol). The reaction covered with aluminum foil, stirred 18 hours at room temperature and refluxed 4 hours. The mixture was cooled, centrifuged, liquor removed, and solids reslurred with tetrahydrofuran (40 ml) and centrifuged. The combined clear liquor was evaporated under vacuum and then dried to constant weight under high vacuum. A whitish semi-solid mixture [4.18, theory for $(Cl)_3(CF_3CO_2)_3P_3N_3$ is 4.19 g] was obtained. The tetrahydrofuran insoluble solids were washed with acetone and dried to give 3.25 g. Further treatment of this solid with 15% $HNO_3$ (60 ml) ($CF_3CO_2Ag$ is insoluble in this acid) followed by washing with water and methanol after vacuum drying, 3.14 g (theory=3.24 g for AgCl). The soluble semi-solid showed several significant volatile components in vapor-phase-liquid chromatography indicative of a mixture of poly(chloro-trifluoroacetoxy) cyclophosphazenes.

EXAMPLE 56

Preparation of $(CH_3SO_3Hg)_2O$

A flask was charged with methanol (500 ml), HgO (108 g, 0.50 mol); and $CH_3SO_3H$ (101 g, 0.57 mol) and stirred well under reflux for 2 hours. Methanol (150 ml) was removed by distillation and benzene (200 ml) was added. The mixture was concentrated to about ½ the volume and a mixture of isopropyl alcohol (150 ml) and benzene (250 ml) was added. The mixture was cooled, solid filtered off and washed with isopropyl alcohol-benzene (1v/1v) and vacuum dried at 130° C. for 18 hours. The product (141 g, 93% yield) was obtained as a whitish solid. Anal. Calcd. for $(CH_3SO_3Hg)_2O$: C, 4.0; H, 1.0; S, 10.5. Found: C, 4.5 H, 1.0; S, 10.7. Anal. Calcd. for $(CH_3SO_3)_2Hg$: C, 6.1; H, 1.5; S, 16.4.

We claim:

1. A catalyst for the polymerization of dihalophosphazenes comprising a substituted cyclophosphazene represented by the formula $(X)_y(PN)_m(An)_z$ wherein m is a positive integer from 3 to 7, y and z are positive integers the sum of y plus z being equal to 2m and z being at least 1;

X is a halogen selected from the group consisting of Cl, Br and F;

An is an monovalent radical selected from the group consisting of

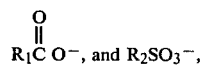
$R_1CO^-$, and $R_2SO_3^-$, where $R_1$ is a monovalent radical selected from the group consisting of polyhaloalkyl where the halogen is F, Cl or mixtures thereof, perfluoraryl and perchloroaryl;

$R_2$ is a monovalent radical selected from the group consisting of F, Cl, lower alkyl ($C_1$–$C_5$), aryl, substituted alkyl and substituted aryl and all of the monovalent radicals are not required to be identical, and for phosphazenes containing two or more X's all of the X's need not be identical; and wherein said substitued cyclophosphazenes are phosphazene derivatives consisting of the reaction product formed by reacting at least one cyclophosphazene represented by the formula $(X_2PN)_m$ in which X represents a halogen selected from the group consisting of F, Cl and Br and in which not all of the X's are required to be the same, and m is an integer of 3 to 7, with at least one metallic or quaternary salt of said monovalent radical $R_1COO-$ or monovalent radical $R_2SO_3-$ and wherein at least one X in the compound $(X_2PN)_m$ is replaced, and all of the displacing groups and X groups are not required to be the same.

2. The catalyst of claim 1 wherein m is 3 or 4 and z is 1 or 2.

3. The catalyst of claim 2 wherein X is Cl.

4. The catalyst of claim 1 wherein An is RCOO—.

5. The catalyst of claim 1 wherein An is $R_2SO_3$—.

6. The catalyst of claim 1 wherein the catalyst is a substituted cyclophosphazene in which at least one substituent is a monovalent radical represented by $R_2SO_3-$ in which $R_2$ is selected from the group consisting of: lower alkyl, perfluoromethyl, perfluorophenyl, fluoro-, chloro-, phenyl-, toluoyl-, naphthyl-, p-bromophenyl-, nitrophenyl-, 2,4-dinitrophenyl-, biphenyl-, and m-$(HO_3S)$phenyl-.

7. The catalyst of claim 1 wherein the catalyst is a substituted cyclophosphazene in which at least one substituent is a monovalent radical represented by the formula $R_1COO-$ in which $R_1$ is selected from the group consisting of: perfluoroaryl trifluoromethyl-, trichloromethyl-, difluoromethyl-, difluorochloromethyl-, perfluoropropyl-, and perfluorobutyl.

8. The catalyst which is the product of reacting $(Cl_2PN)_3$ with $(CH_3SO_3Hg)_2O$.

9. The catalyst which is the product of reacting $(Cl_2PN)_3$ with silver trifluoroacetate.

* * * * *